(12) United States Patent
Avory et al.

(10) Patent No.: US 9,138,493 B2
(45) Date of Patent: Sep. 22, 2015

(54) RADIOIODINATED FATTY ACIDS

(75) Inventors: Michelle E Avory, Wendover (GB); Harry John Wadsworth, Stortford (GB); Robert James Domett Nairne, Amersham (GB)

(73) Assignee: GE Healthcare Limited, Buckinghamshire (GB)

( * ) Notice: Subject to any disclaimer, the term of this patent is extended or adjusted under 35 U.S.C. 154(b) by 0 days.

(21) Appl. No.: 13/993,473

(22) PCT Filed: Dec. 15, 2011

(86) PCT No.: PCT/EP2011/072993
§ 371 (c)(1),
(2), (4) Date: Jun. 12, 2013

(87) PCT Pub. No.: WO2012/080434
PCT Pub. Date: Jun. 21, 2012

(65) Prior Publication Data
US 2013/0272960 A1    Oct. 17, 2013

Related U.S. Application Data

(60) Provisional application No. 61/423,639, filed on Dec. 16, 2010.

(30) Foreign Application Priority Data

Dec. 16, 2010  (GB) .................................. 1021369.2

(51) Int. Cl.
*A61K 51/04* (2006.01)
(52) U.S. Cl.
CPC ......... *A61K 51/0453* (2013.01); *A61K 51/0402* (2013.01); *A61K 51/0497* (2013.01)
(58) Field of Classification Search
CPC ........... A61K 51/0402; A61K 51/0453; A61K 51/0497
See application file for complete search history.

(56) References Cited

FOREIGN PATENT DOCUMENTS

| WO | 2006/067376 | 6/2006 |
| WO | 2007/148089 | 12/2007 |
| WO | 2009/011880 | 1/2009 |
| WO | 2010/129572 | 11/2010 |
| WO | WO 2010129572 A2 * | 11/2010 |
| WO | 2011/020907 | 2/2011 |

OTHER PUBLICATIONS

Goodman, M.M.; Kirsch, G.; Knapp F.F. "Synthesis and Evaluation of Radioiodinated Terminal p-Iodophenyl-Substituted a- and b-Methyl-Branched Fatty Acids" J. Med. Chem. 1984, 27, 390-397.*
Goodman, Journal of Heterocyclic Chemistry, vol. 21, 1984 pp. 1579-1583.
Taki, European Journal of Nucleare Medicine and Molecular Imaging, vol. 34, No. 1, Jun. 2007, pp. S34-S38.
Eersels, Journal Lab. Comp. Radiopharm, vol. 48, 2005 pp. 241-257.
Ito, Bioorganic & Medicinal Chemistry, vol. 16, No. 22, Nov. 2008, pp. 9817-9829.
Kabalka, Journal of Labelled Compounds and Radiopharmaceuticals, vol. 48, No. 5, Apr. 1, 2005,k pp. 359-362.
Kabalka, Journal of Labelled Compounds and Radiopharmacueitcals, bol. 50, No. 5-6, Apr. 1, 2007, pp. 446-447.
PCT/EP2011/072993 ISRWO Dated Apr. 5, 2012.
GB1021369.2 Search Report Dated Mar. 16, 2011.

* cited by examiner

*Primary Examiner* — Sean Basquill
*Assistant Examiner* — Andrew S Rosenthal
(74) *Attorney, Agent, or Firm* — Parks Wood LLC; Collen A. Beard, Esq.

(57) ABSTRACT

The present invention provides novel radioiodinated fatty acids. Also provided are methods of preparation of said radioiodinated fatty acids from non-radioactive precursors, as well as radiopharmaceutical compositions comprising such radioiodinated fatty acids. The invention also provides in vivo imaging methods using the radioiodinated fatty acids.

6 Claims, No Drawings

RADIOIODINATED FATTY ACIDS

This application is a filing under 35 U.S.C. 371 of international application number PCT/EP2011/072993, filed Dec. 15, 2011, which claims priority to Great Britain application number 1021369.2 filed Dec. 16, 2010 and to U.S. application No. 61/423,639 filed Dec. 16, 2010, the entire disclosure of each of which is hereby incorporated by reference.

FIELD OF THE INVENTION

The present invention provides novel radioiodinated fatty acids. Also provided are methods of preparation of said radioiodinated fatty acids from non-radioactive precursors, as well as radiopharmaceutical compositions comprising such radioiodinated fatty acids. The invention also provides in vivo imaging methods using the radioiodinated fatty acids.

BACKGROUND TO THE INVENTION

Under normal conditions, the human heart derives more than 60% of its energy from the oxidative metabolism of long chain fatty acids. In the ischaemic myocardium, however, oxidative metabolism of free fatty acids is suppressed, and anaerobic glucose metabolism predominates. Metabolic imaging can therefore provide useful information in the diagnosis and monitoring of various forms of heart disease.

Fatty acids have been radiolabelled with $^{11}$C and $^{18}$F for PET imaging, and $^{123}$I and $^{99m}$Tc for SPECT radiopharmaceutical imaging [Eckelman et al, J. Nucl. Cardiol., 14, S100-S109 (2007)]. Eckelman et al stress that radiolabelling with an isotope other than $^{11}$C is in fact labelling a fatty acid analogue, and that care is needed that the substituent does not affect the ability of the analogue to trace important steps of the metabolic pathway.

Taki et al [Eur. J. Nucl. Med. Mol. Imaging, 34, S34-S48 (2007)] point out that early radioiodinated fatty acid analogues based on iodo-alkyl substituents were found to suffer significant in vivo metabolic deioidination. Radioiodinated fatty acid analogues incorporating iodo-phenyl moieties such as $^{123}$I-BMIPP and $^{123}$I-IPPA have, however, become established agents for such metabolic imaging (Taki et al, cited above):

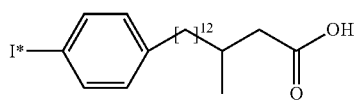

BMIPP

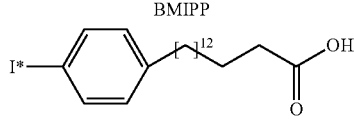

IPPA where I*=$^{123}$I.

The applications of "click chemistry" in biomedical research, including radiochemistry, have been reviewed by Nwe et al [Cancer Biother. Radiopharm., 24(3), 289-302 (2009)]. As noted therein, the main interest has been in the PET radioisotope $^{18}$F (and to a lesser extent $^{11}$C), plus "click to chelate" approaches for radiometals suitable for SPECT imaging such as $^{99m}$Tc or $^{111}$In. $^{18}$F click-labelling of targeting peptides, giving products incorporating an $^{18}$F-fluoro-alkyl-substituted triazole have been reported by Li et al [Bioconj. Chem., 18(6), 1987-1994 (2007)], and Hausner et al [J. Med. Chem., 51(19), 5901-5904 (2008)].

WO 2006/067376 discloses a method for labelling a vector comprising reaction of a compound of formula (I) with a compound of formula (II):

 (I)

 (II)

a compound of formula (III) with a compound of formula (IV)

 (III)

 (IV)

in the presence of a Cu(I) catalyst, to give a conjugate of formula (V) or (VI) respectively:

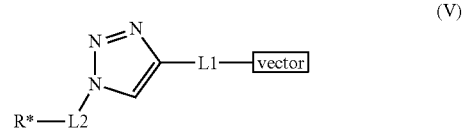 (V)

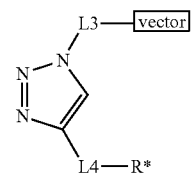 (VI)

wherein L1, L2, L3, and L4 are each Linker groups;
R* is a reporter moiety which comprises a radionuclide.

R* of WO 2006/067376 is a reporter moiety which comprises a radionuclide for example a positron-emitting radionuclide. Suitable positron-emitting radionuclides for this purpose are said to include $^{11}$C, $^{18}$F, $^{75}$Br, $^{76}$Br, $^{124}$I, $^{82}$Rb, $^{68}$Ga, $^{64}$Cu and $^{62}$Cu, of which $^{11}$C and $^{18}$F are preferred. Other useful radionuclides are stated to include $^{123}$I, $^{125}$I, $^{131}$I, $^{211}$At, $^{99m}$Tc, and $^{111}$In.

WO 2007/148089 discloses a method for radiolabelling a vector comprising reaction of a compound of formula (I) with a compound of formula (II):

 (I)

 (II)

or, a compound of formula (III) with a compound of formula (IV):

 (III)

 (IV)

in the presence of a Cu(I) catalyst to give a conjugate of formula (V) or (VI) respectively:

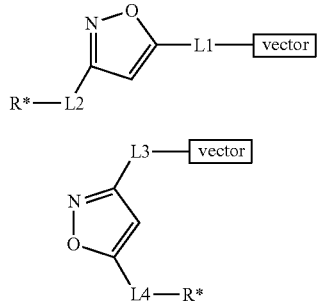

(V)

(VI)

wherein:

L1, L2, L3, and L4 are each Linker groups;

R* is a reporter moiety which comprises a radionuclide.

In both WO 2006/067376 and WO 2007/148089, metallic radionuclides are stated to be suitably incorporated into a chelating agent, for example by direct incorporation by methods known to the person skilled in the art.

WO 2006/116629 (Siemens Medical Solutions USA, Inc.) discloses a method of preparation of a radiolabelled ligand or substrate having affinity for a target biomacromolecule, the method comprising:

(a) reacting a first compound comprising
   (i) a first molecular structure;
   (ii) a leaving group;
   (iii) a first functional group capable of participating in a click chemistry reaction; and optionally,
   (iv) a linker between the first functional group and the molecular structure, with a radioactive reagent under conditions sufficient to displace the leaving group with a radioactive component of the radioactive reagent to form a first radioactive compound;

(b) providing a second compound comprising
   (i) a second molecular structure;
   (ii) a second complementary functional group capable of participating in a click chemistry reaction with the first functional group, wherein the second compound optionally comprises a linker between the second compound and the second functional group;

(c) reacting the first functional group of the first radioactive compound with the complementary functional group of the second compound via a click chemistry reaction to form the radioactive ligand or substrate; and (d) isolating the radioactive ligand or substrate.

WO 2006/116629 teaches that the method therein is suitable for use with the radioisotopes: $^{124}$I, $^{18}$F, $^{11}$C, $^{13}$N and $^{15}$O with preferred radioisotopes being: $^{18}$F, $^{11}$C, $^{123}$I, $^{124}$I, $^{127}$I, $^{131}$I, $^{76}$Br, $^{64}$Cu, $^{99m}$TC, $^{90}$Y, $^{67}$Ga, $^{51}$Cr, $^{192}$Ir, $^{99}$Mo, $^{153}$Sm and $^{201}$Tl. WO 2006/116629 teaches that other radioisotopes that may be employed include: $^{72}$As, $^{74}$As, $^{75}$Br, $^{55}$Co, $^{61}$Cu, $^{67}$Cu, $^{68}$Ga, $^{68}$Ge, $^{125}$I, $^{132}$I, $^{111}$In, $^{52}$Mn, $^{203}$Pb and $^{97}$Ru. WO 2006/116629 does not, however, provide any specific teaching on how to apply the method to the radioiodination of biological molecules.

WO 2010/129572 describes PET radiotracers for imaging fatty acid metabolism and storage having one of the following formulae:

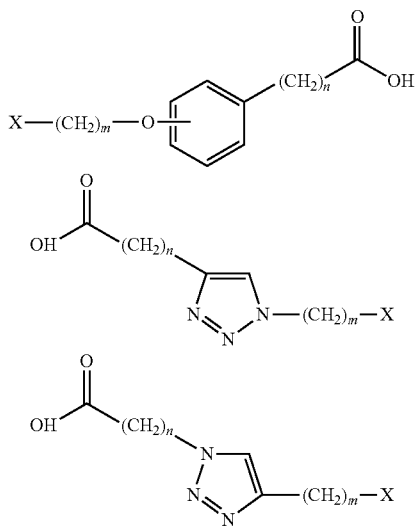

where: n is 10-24, m is 1-10 and X is a halogen.

WO 2010/129572 teaches that at least one atom of the above chemical structures can be a radionuclide, preferably a positron-emitting radioisotope. $^{18}$F is the main radioisotope described. The structures shown would not be expected to be suitable for labelling with radioiodine, since if X were to be iodine that requires an iodoalkyl group, and such groups are known to be unstable with respect to deiodination in vivo.

Kim et al [Bioconj. Chem., 20(6), 1139-1145 (2009) disclose $^{18}$F-labelled fatty acid analogues for PET imaging of myocardial metabolism:

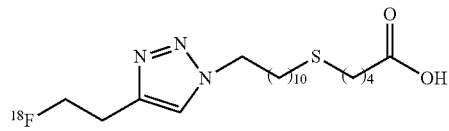

The $^{18}$F-fatty acids were prepared via click cycloaddition, wherein an $^{18}$F-alkyne was coupled to an azido-fatty acid, to generate the triazole ring.

PET imaging with $^{18}$F typically requires the availability of a cyclotron facility on the same site as the hospital, since $^{18}$F has a short half-life (110 minutes) and the desired radiotracer needs to be synthesised. The availability of cameras suitable for PET imaging is consequently much less widespread than SPECT cameras. There is therefore still a need for alternative radioiodinated fatty acids suitable for more routine clinical imaging, especially using SPECT radiopharmaceutical imaging.

The longer half-life of $^{123}$I compared to $^{18}$F enables the cyclotron for its production to be up to one day's transport time from the end user. This makes it possible for a single cyclotron to be able to supply a continent rather than a city, as is the case with $^{18}$F fluorine production.

The Present Invention

The present invention provides radioiodinated fatty acid analogues comprising triazole or isoxazole rings. The triazole and isoxazole rings do not hydrolyse and are highly stable to oxidation and reduction, meaning that the labelled fatty acid has high in vivo stability. The triazole ring is also comparable to an amide in size and polarity. The triazole and isoxazole rings of the fatty acids of Formula (I) of the present invention are not expected to be recognized by thyroid deiodination enzymes known to metabolise iodo-tyrosine more rapidly than iodobenzene, and are thus expected to be sufficiently stable in vivo for radiopharmaceutical imaging and/or radiotherapy.

When the iodine isotope is $^{123}$I or $^{131}$I, the fatty acids of the present invention have the advantage that they are suitable for SPECT imaging, and hence have a wider clinical potential than PET agents, due to the wider availability of gamma cameras. The radioiodinated fatty acid analogues can be synthesised readily using either click chemistry, or organometallic precursors. Mild reaction conditions are required for the synthesis of the carbon iodine bond and this enables sensitive molecules to be radioiodinated. In general radiofluorination requires much more forcing conditions rendering it unsuitable for very sensitive molecules.

DETAILED DESCRIPTION OF THE INVENTION

In a first aspect, the present invention provides a radioiodinated fatty acid of Formula (I):

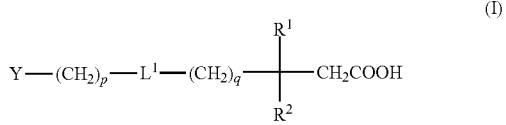

(I)

where:
$R^1$ and $R^2$ are independently H or $C_{1-2}$ alkyl;
Y is a $Y^1$ or $Y^2$ group:

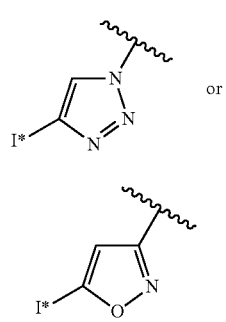

p and q are each independently integers of value 0 to 10 which are chosen such that [p+q] is in the range 10 to 16;
$L^1$ is a linker group of formula -(A)$_n$- where n is an integer of value 0 to 3, and each A group is independently chosen from —CH$_2$—, —O—, —S— and —C$_6$H$_4$— with the proviso that $L^1$ does not comprise —O—O—, —S—S— or —O—S— linkages;
I* is a radioisotope of iodine.

The term "radioiodinated" has its conventional meaning, i.e. a radiolabelled compound wherein the radioisotope used for the radiolabelling is a radioisotope of iodine. The term "radioisotope of iodine" has its conventional meaning, i.e. an isotope of the element iodine that is radioactive. Suitable such radioisotopes include: $^{123}$I, $^{124}$I, $^{125}$I and $^{131}$I.

The term "fatty acid" has its conventional meaning, i.e. a monobasic aliphatic carboxylic acid, typically having at least a 10-carbon chain.

Preferred Aspects.

Preferred radioisotopes of iodine for use in the present invention are those suitable for medical imaging in vivo using PET or SPECT, preferably $^{123}$I, $^{124}$I or $^{131}$I, more preferably $^{123}$I or $^{124}$I, most preferably $^{123}$I.

A preferred radioiodinated fatty acid of the first aspect is where Y is $Y^1$, i.e. the radioiodine isotope is attached to a triazole ring.

In Formula (I), preferably at least one of $R^1$ and $R^2$ is $C_{1-2}$ alkyl, more preferably methyl. Most preferably, $R^1$ is CH$_3$ and $R^2$ is H.

In Formula (I), $L^1$ is preferably chosen from —CH$_2$—, —O— and —S—. In Formula (I), n is preferably 0. In Formula (I), [p+q] is preferably in the range 10 to 14. When n=0, [p+q] is preferably in the range 11 to 14, more preferably 11 to 13.

The radioiodinated fatty acids of Formula (I) may be obtained as described in the second or third aspects (below). The preparation method of the second aspect (via Precursor IA) is preferred, since that comprises only a single step in which radioactive manipulations are involved (a single step iododemetallation reaction)—thus minimising the radiation dose to the operator.

Included within the scope of the first aspect is an imaging agent which comprises the radioiodinated fatty acid of Formula (I). By the term "imaging agent" is meant a compound suitable for imaging the mammalian body. Preferably, the mammal is an intact mammalian body in vivo, and is more preferably a human subject. Preferably, the imaging agent can be administered to the mammalian body in a minimally invasive manner, i.e. without a substantial health risk to the mammalian subject when carried out under professional medical expertise. Such minimally invasive administration is preferably intravenous administration into a peripheral vein of said subject, without the need for local or general anaesthetic. The imaging agents of the first aspect are preferably used as radiopharmaceutical compositions, as described in the fourth aspect (below).

In a second aspect, the present invention a method of preparation of the radioiodinated fatty acid of Formula (I) of the first aspect, where said method comprises:

(i) provision of a precursor of Formula (IA)

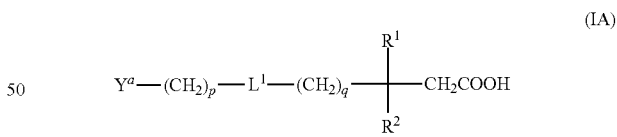

(IA)

where:
$R^1$, $R^2$, $L^1$, p and q are as defined in any one of claims 1 to 6;
$Y^a$ is a $Y^{1a}$ or $Y^{2a}$ group:

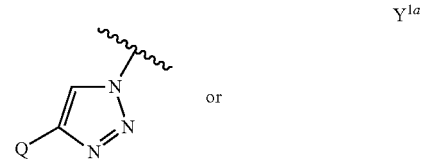

$Y^{1a}$

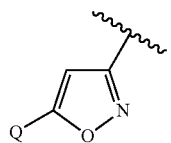

wherein Q is $R^a{}_3Sn$— or $KF_3B$—, where each $R^a$ is independently $C_{1-4}$ alkyl;

(ii) reaction of said precursor with radioactive iodide ion in the presence of an oxidising agent to give the radioiodinated fatty acid of Formula (I).

Preferred embodiments of $R^1$, $R^2$, $L^1$, p and q and I* in the second aspect are as defined in the first aspect.

In $Y^a$, when Q is $KF_3B$—, that corresponds to a potassium trifluoroborate derivative as described below.

By the term "oxidising agent" is meant an oxidant capable of oxidising iodide ion to form the electrophilic species (HOI, $H_2OI$), wherein the active iodinating agent is $I^+$. Suitable oxidising agents are described by Bolton [J. Lab. Comp. Radiopharm., 45, 485-528 (2002)], and Eersels et al [J. Lab. Comp. Radiopharm., 48, 241-257 (2005)] and include peracetic acid and N-chloro compounds, such as chloramine-T, iodogen, iodogen tubes and succinimides. Preferred oxidising agents are peracetic acid (which is commercially available) at pH ca. 4, and hydrogen peroxide/aqueous HCl at pH ca. 1. Iodogen tubes are commercially available from Thermo Scientific Pierce Protein Research Products.

By the term "radioactive iodide ion" is meant a radioisotope of iodine (as defined above), in the chemical form of iodide ion (F).

When Q is $R^a{}_3Sn$—, the radioiodination method of the third aspect is carried out as described by Bolton [J. Lab. Comp. Radiopharm., 45, 485-528 (2002)] and Eersels et al [J. Lab. Comp. Radiopharm., 48, 241-257 (2005)]. The organotin precursors are prepared as described by Ali et al [Synthesis, 423-445 (1996)].

When Q is $KF_3B$—, the radioiodination reaction method of the third aspect can be carried out as described by Kabalka et al [J. Lab. Comp. Radiopharm., 48, 359-362 (2005)], who use peracetic acid as the oxidising agent. Precursors where Q is $KF_3B$— can be obtained from the corresponding alkyne as described by Kabalka et al [J. Lab. Comp. Radiopharm., 48, 359-362 (2005) and, J. Lab. Comp. Radiopharm., 49, 11-15 (2006)]. The potassium trifluoroborate precursors are stated to be crystalline solids, which are stable to both air and water.

The radioiodination reaction of the second aspect may be effected in a suitable solvent, for example acetonitrile, a $C_{1-4}$ alkylalcohol, dimethylformamide, tetrahydrofuran (THF), or dimethylsulfoxide, or mixtures thereof, or aqueous mixtures thereof, or in water. Aqueous buffers can also be used. The pH will depend on the oxidant used, and will typically be pH 0 to 1 when eg. hydrogen peroxide/aqueous acid is used, or in the range pH 6-8 when iodogen or iodogen tubes are used. The radioiodination reaction temperature is preferably 10 to 60° C., more preferably at 15 to 50° C., most preferably at ambient temperature (typically 15-37° C.). Organic solvents such as acetonitrile or THF and/or the use of more elevated temperature may conveniently be used to solubilise any precursors of Formula (TB) which are poorly soluble in water.

The precursor of Formula (IA) is suitably non-radioactive, so can be prepared and purified by conventional means without the need for radiation handling safety precautions.

In a third aspect, the present invention provides a method of preparation of the radioiodinated fatty acid of Formula (I) as defined in the first aspect, where said method comprises:

(i) provision of a precursor of Formula (IB)

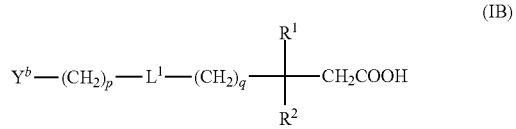

where:
$R^1$, $R^2$, $L^1$, p and q are as defined in any one of claims 1 to 6;
$Y^b$ is a $Y^{1b}$ or $Y^{2b}$ group:

(ii) reaction of said precursor with a compound of Formula (II):

in the presence of a click cycloaddition catalyst, to give the radioiodinated fatty acid of Formula (I) via click cycloaddition,
wherein I* is a radioisotope of iodine, as defined in claim 1 or claim 2.

In Formula (IB), Y can be either an azide substituent ($Y=Y^{1a}$), or an isonitrile oxide substituent ($Y=Y^{2a}$).

Preferred embodiments of $R^1$, $R^2$, $L^1$, p and q and I* in the third aspect are as defined in the first aspect.

By the term "click cycloaddition catalyst" is meant a catalyst known to catalyse the click (alkyne plus azide) or click (alkyne plus isonitrile oxide) cycloaddition reaction. Suitable such catalysts are known in the art for use in click cycloaddition reactions. Preferred such catalysts include Cu(I), and are described below. Further details of suitable catalysts are described by Wu and Fokin [Aldrichim. Acta, 40(1), 7-17 (2007)] and Meldal and Tornoe [Chem. Rev., 108, 2952-3015 (2008)]. The applications of "click chemistry" in biomedical research, including radiochemistry, have been reviewed by Nwe et al [Cancer Biother. Radiopharm., 24(3), 289-302 (2009)].

A preferred click cycloaddition catalyst comprises Cu(I). The Cu(I) catalyst is present in an amount sufficient for the reaction to progress, typically either in a catalytic amount or in excess, such as 0.02 to 1.5 molar equivalents relative to the compound of Formula (Ia) or (Ib). Suitable Cu(I) catalysts include Cu(I) salts such as CuI or $[Cu(NCCH_3)_4][PF_6]$, but advantageously Cu(II) salts such as copper (II) sulphate may be used in the presence of a reducing agent to generate Cu(I) in situ. Suitable reducing agents include: ascorbic acid or a salt thereof for example sodium ascorbate, hydroquinone, metallic copper, glutathione, cysteine, $Fe^{2+}$, or $Co^{2+}$. Cu(I) is also intrinsically present on the surface of elemental copper particles, thus elemental copper, for example in the form of powder or granules may also be used as catalyst. Elemental copper, with a controlled particle size is a preferred source of the Cu(I) catalyst. A more preferred such catalyst is elemental copper as copper powder, having a particle size in the range 0.001 to 1 mm, preferably 0.1 mm to 0.7 mm, more preferably around 0.4 mm. Alternatively, coiled copper wire can be used with a diameter in the range of 0.01 to 1.0 mm, preferably 0.05 to 0.5 mm, and more preferably with a diameter of 0.1 mm. The Cu(I) catalyst may optionally be used in the presence of bathophenanthroline, which is used to stabilise Cu(I) in click chemistry.

In the method of the third aspect, the compound of Formula (II) may optionally be generated in situ by deprotection of a compound of Formula (IIa):

(IIa)

wherein $M^1$ is an alkyne-protecting group, and I* is as defined for Formula (II). Preferred aspects of I* in Formula (IIa), are as described for Formula (II).

By the term "protecting group" is meant a group which inhibits or suppresses undesirable chemical reactions, but which is designed to be sufficiently reactive that it may be cleaved from the functional group in question under mild enough conditions that do not modify the rest of the molecule. After deprotection the desired product is obtained. Suitable alkyne protecting groups are described in *Protective Groups in Organic Synthesis*, Theodora W. Greene and Peter G. M. Wuts, Chapter 8, pages 927-933, 4$^{th}$ edition (John Wiley & Sons, 2007), and include: an trialkylsilyl group where each alkyl group is independently $C_{1-4}$ alkyl; an aryldialkylsilyl group where the aryl group is preferably benzyl or biphenyl and the alkyl groups are each independently $C_{1-4}$ alkyl; hydroxymethyl or 2-(2-hydroxypropyl). A preferred such alkyne protecting group is trimethylsilyl. The protected iodoalkynes of Formula (IIa) have the advantages that the volatility of the radioactive iodoalkyne can be controlled, and that the desired alkyne of Formula (II) can be generated in a controlled manner in situ so that the efficiency of the reaction with the precursor of Formula (IA) is maximised.

The click cycloaddition method of the second aspect may be effected in a suitable solvent, for example acetonitrile, a $C_{1-4}$alkylalcohol, dimethylformamide, tetrahydrofuran, or dimethylsulfoxide, or aqueous mixtures of any thereof, or in water. Aqueous buffers can be used in the pH range of 4-8, more preferably 5-7. The reaction temperature is preferably 5 to 100° C., more preferably at 75 to 85° C., most preferably at ambient temperature (typically 15-37° C.). The click cycloaddition may optionally be carried out in the presence of an organic base, as is described by Meldal and Tornoe [Chem. Rev. 108 2952, Table 1 (2008)].

A preferred precursor of Formula (IB) has $Y^b=Y^{1b}$. One reason is that the isonitrile oxides are typically less stable than azides. Consequently, whilst the azide of Formula (IB, $Y^b=Y^{1b}$) can be isolated and purified, the isonitrile oxide of Formula (IB, $Y^b=Y^{2b}$) will typically need to be generated in situ.

The non-radioactive precursor compound of Formula (IB), where $Y^b$ is $Y^{1b}$ (azido derivatives) may be prepared by either:
(i) reaction of the corresponding bromo-fatty acid with sodium azide;
(ii) conversion of the corresponding hydroxy-fatty acid to a tosylate or mesylate derivative, and subsequent reaction with sodium azide.

Further details are provided by Kim et al [Bioconj. Chem., 20(6), 1139-1145 (2009)], and Kostiuk et al [Meth. Enzymol., 457, 149-165 (2009)]. Many functionalised fatty acids are commercially available.

The non-radioactive precursor compound of Formula (IB), where $Y^b$ is $Y^{2b}$ (isonitrile oxide derivatives) may be prepared by the methods described by Ku et al [Org. Lett., 3(26), 4185-4187 (2001)], and references therein. Thus, they are typically generated in situ by treatment of an alpha-halo aldoxime with an organic base such as triethylamine. A preferred method of generation, as well as conditions for the subsequent click cyclisation to the desired isoxazole are described by Hansen et al [J. Org. Chem., 70(19), 7761-7764 (2005)]. Hansen et al generate the desired alpha-halo aldoxime in situ by reaction of the corresponding aldoxime with chloramine-T trihydrate, and then dechlorinating this with sodium hydroxide. The corresponding aldoxime is prepared by reacting the corresponding aldehyde with hydroxylamine hydrochloride at pH 9-10. See also K. B. G. Torsell *Nitrite Oxides, Nitrones and Nitronates in Organic Synthesis* [VCH, New York (1988)]. Ω-aldehyde functionalised fatty acids are readily accessible by the oxidation of the corresponding alcohol in a Swern oxidation. The alcohols are generally commercially available but are also accessible by ozone oxidation to the ozonide of the corresponding unsatuturated fatty acid followed by borohydride reduction to the alcohol. A very wide range of unsaturated fatty acids are available from natural product sources.

Included within the scope of this third aspect, is the option of using an aldoxime precursor, wherein instead of $Y^{2b}$, $Y^b$ is chosen to be (HO)N=CH—, so that the $Y^{2b}$) isonitrile oxide ($Y^b=Y^{2b}$) is generated in situ. The steps involved can be carried out sequentially without workup. The resulting nitrile oxide is not particularly stable and is best used immediately, preferably in situ without workup.

The preparation methods of the second and third aspects are preferably carried out in an aseptic manner, such that the product of Formula (I) is obtained as a radiopharmaceutical composition. Thus, the method is carried out under aseptic manufacture conditions to give the desired sterile, non-pyrogenic radiopharmaceutical product. It is preferred therefore that the key components, especially any parts of the apparatus which come into contact with the product of Formula (I) (e.g. vials and transfer tubing) are sterile. The components and reagents can be sterilised by methods known in the art, including: sterile filtration, terminal sterilisation using e.g. gamma-irradiation, autoclaving, dry heat or chemical treatment (e.g. with ethylene oxide). It is preferred to sterilise the non-radioactive components in advance, so that the minimum number of manipulations need to be carried out on the radioiodinated radiopharmaceutical product. As a precaution, however, it is preferred to include at least a final sterile filtration step.

The precursors of Formula (IA) or (IB), and other reactants, reagents and solvents are each supplied in suitable vials or vessels which comprise a sealed container which permits maintenance of sterile integrity and/or radioactive safety, plus optionally an inert headspace gas (eg. nitrogen or argon), whilst permitting addition and withdrawal of solutions by syringe or cannula. A preferred such container is a septum-sealed vial, wherein the gas-tight closure is crimped on with an overseal (typically of aluminium). The closure is suitable for single or multiple puncturing with a hypodermic needle (e.g. a crimped-on septum seal closure) whilst maintaining sterile integrity. Such containers have the additional advantage that the closure can withstand vacuum if desired (eg. to change the headspace gas or degas solutions), and withstand pressure changes such as reductions in pressure without permitting ingress of external atmospheric gases, such as oxygen or water vapour. The reaction vessel is suitably chosen from such containers, and preferred embodiments thereof. The reaction vessel is preferably made of a biocompatible plastic (eg. PEEK).

When the radioiodinated fatty acid is used as a pharmaceutical composition, the method of the second or third aspects is preferably carried out using an automated synthesizer apparatus. By the term "automated synthesizer" is meant an automated module based on the principle of unit operations as described by Satyamurthy et al [Clin. Positr. Imag., 2(5), 233-253 (1999)]. The term 'unit operations' means that complex processes are reduced to a series of simple operations or reactions, which can be applied to a range of materials. Such automated synthesizers are preferred for the method of the present invention especially when a radiopharmaceutical product is desired. They are commercially available from a range of suppliers [Satyamurthy et al, above], including: GE Healthcare; CTI Inc; Ion Beam Applications S.A. (Chemin du Cyclotron 3, B-1348 Louvain-La-Neuve, Belgium); Raytest (Germany) and Bioscan (USA).

Commercial automated synthesizers also provide suitable containers for the liquid radioactive waste generated as a result of the radiopharmaceutical preparation. Automated synthesizers are not typically provided with radiation shielding, since they are designed to be employed in a suitably configured radioactive work cell. The radioactive work cell provides suitable radiation shielding to protect the operator from potential radiation dose, as well as ventilation to remove chemical and/or radioactive vapours. The automated synthesizer preferably comprises a cassette.

By the term "cassette" is meant a piece of apparatus designed to fit removably and interchangeably onto an automated synthesizer apparatus (as defined below), in such a way that mechanical movement of moving parts of the synthesizer controls the operation of the cassette from outside the cassette, i.e. externally. Suitable cassettes comprise a linear array of valves, each linked to a port where reagents or vials can be attached, by either needle puncture of an inverted septum-sealed vial, or by gas-tight, marrying joints. Each valve has a male-female joint which interfaces with a corresponding moving arm of the automated synthesizer. External rotation of the arm thus controls the opening or closing of the valve when the cassette is attached to the automated synthesizer. Additional moving parts of the automated synthesizer are designed to clip onto syringe plunger tips, and thus raise or depress syringe barrels.

The cassette is versatile, typically having several positions where reagents can be attached, and several suitable for attachment of syringe vials of reagents or chromatography cartridges (eg. solid phase extraction, SPE). The cassette always comprises a reaction vessel. Such reaction vessels are preferably 1 to 10 cm$^3$, most preferably 2 to 5 cm$^3$ in volume and are configured such that 3 or more ports of the cassette are connected thereto, to permit transfer of reagents or solvents from various ports on the cassette. Preferably the cassette has 15 to 40 valves in a linear array, most preferably 20 to 30, with 25 being especially preferred. The valves of the cassette are preferably each identical, and most preferably are 3-way valves. The cassettes of the present invention are designed to be suitable for radiopharmaceutical manufacture and are therefore manufactured from materials which are of pharmaceutical grade and ideally also are resistant to radiolysis.

Preferred automated synthesizers of the present invention are those comprising a disposable or single use cassette which comprises all the reagents, reaction vessels and apparatus necessary to carry out the preparation of a given batch of radioiodinated radiopharmaceutical. The cassette means that the automated synthesizer has the flexibility to be capable of making a variety of different radioiodine-labelled radiopharmaceuticals with minimal risk of cross-contamination, by simply changing the cassette. The cassette approach also has the advantages of: simplified set-up hence reduced risk of operator error; improved GMP (Good Manufacturing Practice) compliance; multi-tracer capability; rapid change between production runs; pre-run automated diagnostic checking of the cassette and reagents; automated barcode cross-check of chemical reagents vs the synthesis to be carried out; reagent traceability; single-use and hence no risk of cross-contamination, tamper and abuse resistance.

In a fourth aspect, the present invention provides a radiopharmaceutical composition comprising an effective amount of the radioiodinated fatty acid of Formula (I) as defined in the first aspect, together with a biocompatible carrier medium.

Preferred embodiments of the radioiodinated fatty acid of Formula (I) in the fourth aspect are as defined in the first aspect.

The "biocompatible carrier medium" comprises one or more pharmaceutically acceptable adjuvants, excipients or diluents. It is preferably a fluid, especially a liquid, in which the radioiodinated fatty acid of Formula (I) is suspended or dissolved, such that the composition is physiologically tolerable, i.e. can be administered to the mammalian body without toxicity or undue discomfort. The biocompatible carrier medium is suitably an injectable carrier liquid such as sterile, pyrogen-free water for injection; an aqueous solution such as saline (which may advantageously be balanced so that the final product for injection is either isotonic or not hypotonic); an aqueous solution of one or more tonicity-adjusting substances (eg. salts of plasma cations with biocompatible counterions), sugars (e.g. glucose or sucrose), sugar alcohols (eg. sorbitol or mannitol), glycols (eg. glycerol), or other non-ionic polyol materials (eg. polyethyleneglycols, propylene glycols and the like). The biocompatible carrier medium may also comprise biocompatible organic solvents such as ethanol. Such organic solvents are useful to solubilise more lipophilic compounds or formulations. Preferably the biocompatible carrier medium is pyrogen-free water for injection, isotonic saline or an aqueous ethanol solution. The pH of the biocompatible carrier medium for intravenous injection is suitably in the range 4.0 to 10.5.

In a fifth aspect, the present invention provides the use of the precursor of Formula (IA) as defined in the second aspect, or the precursor of Formula (IB) as defined in the third aspect in the manufacture of the radioiodinated fatty acid of Formula (I) as defined in the first aspect, or for the manufacture of the radiopharmaceutical composition of the fourth aspect.

Preferred embodiments of the radioiodinated fatty acid of Formula (I), precursor of Formula (IA) or of Formula (IB) in the use of the fifth aspect, are as defined in the first, second and third aspects respectively.

In a sixth aspect, the present invention provides the use of an automated synthesizer apparatus to carry out the method of preparation of the second or third aspects.

Preferred embodiments of the precursors, methods and automated synthesizer in the use of the sixth aspect are as described in the second and third aspects.

In a seventh aspect, the present invention provides a method of generating an image of a human or animal body comprising administering the radioiodinated fatty acid of Formula (I) of the first aspect, or the radiopharmaceutical composition of the fourth aspect, and generating an image of at least a part of said body to which said compound or composition has distributed using PET or SPECT.

Preferred aspects of the radioiodinated fatty acid and radiopharmaceutical composition in the seventh aspect are as described in the first and fourth aspects respectively.

The radioiodinated fatty acids of the invention are useful for imaging myocardial metabolism, in particular for patients with coronary artery disease. Such imaging includes the imaging of: acute myocardial infarction; unstable angina;

myocardial viability assessment and prediction of recovery of function in chronic coronary artery disease; risk stratification and prognosis. The agent may also be useful, in conjunction with myocardial perfusion assessment for patients with cardiomyopathy. Further details are provided by Taki et al [Eur. J. Nucl. Med. Mol. Imaging, 34, S34-S48 (2007)].

In a further aspect, the present invention provides a method of monitoring the effect of treatment of a human or animal body with a drug, said method comprising administering to said body the radioiodinated fatty acid of Formula (I) as defined in the first aspect, or the radiopharmaceutical composition of the fourth aspect, and detecting the uptake of said fatty acid or composition in at least a part of said body to which said fatty acid or composition has distributed using PET or SPECT, said administration and detection optionally but preferably being effected before, during and after treatment with said drug. The administration and detection of this final aspect are preferably effected before and after treatment with said drug, so that the effect of the drug treatment on the human or animal patient can be determined. Where the drug treatment involves a course of therapy, the imaging can also be carried out during the treatment. The diseases or conditions being treated in the further aspect are as described in the seventh aspect (above)

The invention is illustrated by the following Examples. Example 1 provides the synthesis of $^{123}$I-iodoacetylene. Example 2 provides the click cycloaddition of $^{123}$I-iodoacetylene to an azide derivative, to form a radioiodinated triazole ring. Example 3 provides the click cycloaddition of $^{123}$I-iodoacetylene to an isonitrile oxide derivative, to form a radioiodinated isoxazole ring. Example 4 provides a click cycloaddition of a tributyltin-alkyne to an azide derivative, to form a triazole radioiodination precursor having a triazole-tributyltin bond. Example 5 provides the conditions for converting the precursor of Example 4, to the radioiodinated product. Example 6 provides a synthesis of an isoxazole radioiodination precursor having an isoxazole-tributyltin bond via click cycloaddition from an isonitrile oxide derivative. Example 7 provides the radioiodination of the precursor of Example 6. Example 8 provides the synthesis of an iodotriazole-substituted fatty acid. Example 9 provides the synthesis of an iodoisoxazole-substituted fatty acid.

ABBREVIATIONS USED IN THE EXAMPLES

HPLC: high performance liquid chromatography,
PAA: peracetic acid,
RCP: radiochemical purity,
THF: tetrahydrofuran.

Example 1

Preparation and Distillation of [$^{123}$I]-Iodoacetylene Using Peracetic Acid Oxidant

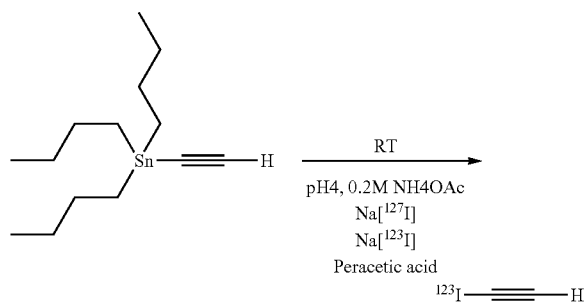

To a Wheaton vial on ice was added, ammonium acetate buffer (100 μl, 0.2M, pH 4), sodium [$^{127}$I] iodide (10 μl, 10 mM solution in 0.01M sodium hydroxide, 1×10$^{-7}$ moles), sodium [$^{123}$I] iodide (20 μl, 53 MBq), peracetic acid, (10 μl, 10 mM solution, 1×10$^{-7}$ moles) and a solution of ethynyl-tributylstannane in THF (Sigma-Aldrich; 38 μl, 1 mg/mL, 1.2×10$^{-7}$ moles). Finally, 460 μl THF was added, the Wheaton vial sealed and the reaction mixture allowed to warm to room temperature prior to reverse phase HPLC analysis which showed [$^{123}$I]-iodoacetylene with a radiochemical purity (RCP) of 75% ($t_R$ 12.3 minutes, System A).

The reaction mixture was heated at 80-100° C. for 30 minutes during which time, the [$^{123}$I]-iodoacetylene and THF were distilled through a short tube into a collection vial on ice. After this time, a low flow of nitrogen was passed through the septa of the heated vial to remove any residual liquids from the tube. [$^{123}$I]-iodoacetylene was collected in 38.6% yield (non decay corrected) with an RCP of 94%. ($t_R$ 12.3 minutes, System A).

| HPLC System A (A = water; B = acetonitrile). Column C18 (2) phenonenex Luna, 150 × 4.6 mm, 5 micron | | | | | | |
|---|---|---|---|---|---|---|
| | | Time (min) | | | | |
| | | 0 | 1 | 20 | 25 | 25.5 | 30 |
| Gradient | % B | 5 | 5 | 95 | 95 | 5 | 5 |

Example 2

Preparation of 1-Benzene-4-[$^{123}$I]-iodo-1H-1,2,3 triazole (Prophetic Example)

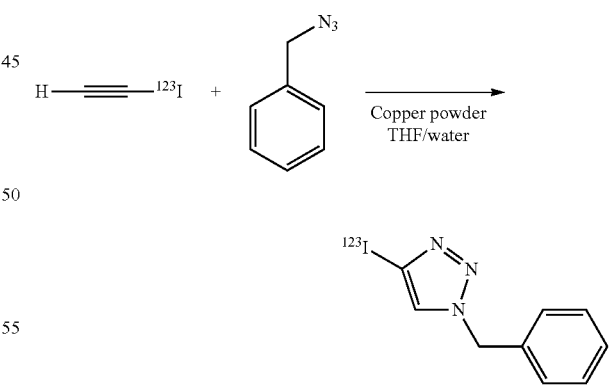

To a Wheaton vial charged with copper powder (200 mg, −40 mesh), sodium phosphate buffer (200 μL, pH 6, 50 mM) and placed on ice is added, [$^{121}$I]-iodoacetylene and benzyl azide (1 mg, 7.5×10$^{-6}$ moles). Following reagent addition, the ice bath is removed and the reaction incubated at room temperature with heating applied as required. 1-Benzene-4-[$^{123}$I]-iodo-1H-1,2,3-triazole is purified by reverse phase HPLC.

Example 3

Preparation of 5-[$^{123}$I]-iodo-3-phenyl isoxazole
(Prophetic Example)

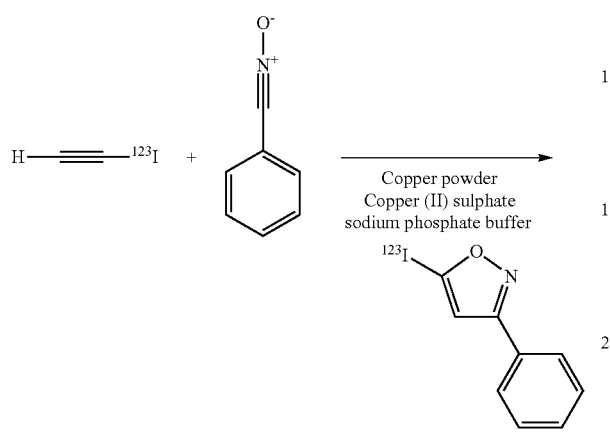

To a Wheaton vial charged with copper powder (50 mg, −40 mesh), copper (II) sulphate (3.8 µg, 1.53×10-8 moles, 0.5 mg/mL solution in water), sodium phosphate buffer (100 µL, 50 mM, pH6) and placed on ice, is added [$^{123}$I]-iodoacetylene and benzonitrile-N-oxide (1 mg, 8.4×10$^{-6}$ moles. Following reagent addition, the ice bath is removed and the reaction incubated at room temperature with heating applied as required. 5-[$^{123}$I]-iodo-3-phenyl isoxazole is purified by reverse phase HPLC.

Example 4

Preparation of 1-Phenyl-4-(tributylstannyl)-1H[1,2,3]triazole
(Prophetic example)

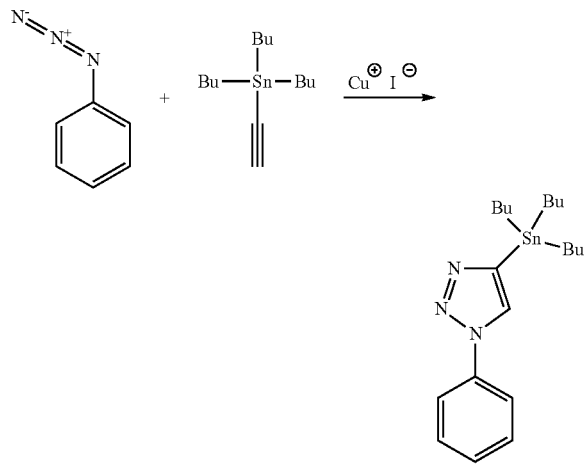

Phenylazide can be obtained from Sigma-Aldrich or can be synthesized by the method described in J. Biochem., 179, 397-405 (1979). A solution of tributylethynyl stannane (Sigma Aldrich; 400 mg, 1.27 mmol) in THF (4 mL) is treated with phenylazide (169 mg, 1.27 mmol), copper (I) iodide (90 mg, 0.47 mmol), and triethylamine (256 mg, 2.54 mmol) at room temperature over 48 h. The reaction is then filtered through celite to remove copper (I) iodide and chromatographed on silica in a gradient of 5-20% ethyl acetate in petrol. The second fraction is collected and concentrated in vacuo to give the 1-phenyl-4-(tributylstannyl)-1H [1,2,3]triazole as a colourless oil.

Example 5

Preparation of [$^{123}$I]-1-Phenyl-4-iodo-1H[1,2,3]triazole Using Peracetic Acid as the Oxidant (Prophetic example)

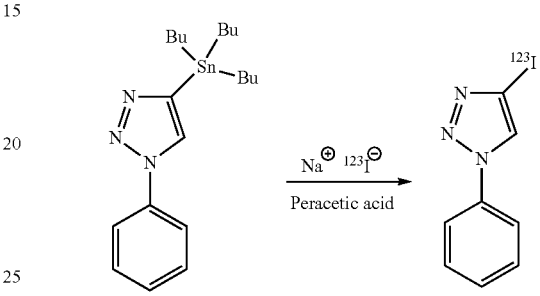

To sodium [$^{123}$I] iodide, received in 5-20 µL 0.05M sodium hydroxide is added ammonium acetate buffer (100 µL pH 4.0, 0.2M), sodium [$^{127}$I] iodide (10 µL 1 mM solution in 0.01M sodium hydroxide, 1×10$^{-8}$ moles), peracetic acid (PAA) solution (10 µL 1 mM solution, 1×10$^{-8}$ moles) and finally, 1 phenyl-4-tributylstannyl-1H [1,2,3]triazole (Example 4; 43 µg, 1×10$^{-7}$ moles) dissolved in acetonitrile. The reaction mixture is incubated at room temperature for 15 minutes prior to purification by HPLC.

Example 6

Preparation of 3-Phenyl-5-(tributylstannyl) isoxazole
(Prophetic example)

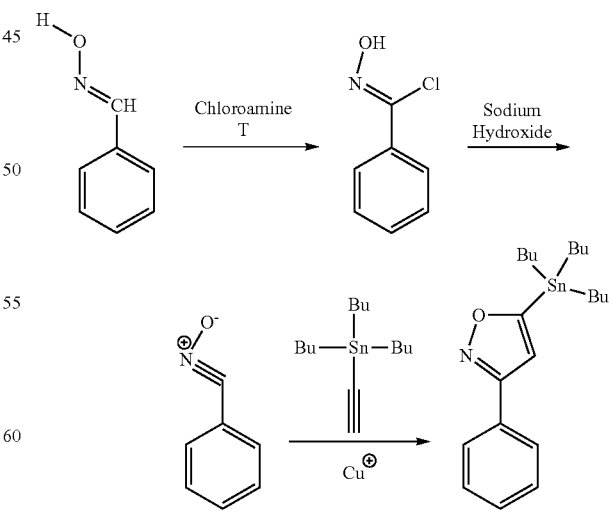

(E)-benzaldehyde oxime (Sigma Aldrich; 3.3 g, 20 mmol) in tert butanol and water (1:1) 80 mL, is treated with chloramine T trihydrate (Sigma Aldrich; 5.9 g, 21 mmol) in small, portions over 5 min. The reaction is then treated with copper sulfate pentahydrate (0.15 g, 0.6 mmol) and copper turnings ~50 mg and tributylethynylstannane (6.3 g, 20 mmol). The reaction is then adjusted to pH 6 with sodium hydroxide solution and stirred for 6 h. The reaction mixture is treated with dilute ammonium hydroxide solution to remove all copper salts. The product is collected by filtration, redissolved in ethyl acetate and filtered through a short plug of silica gel. The filtrate is concentrated in vacuo to give 3-phenyl-5-(tributylstannyl) isoxazole.

Example 7

Preparation of 5-[$^{123}$I]-Iodo-3-phenyl isoxazole (prophetic Example)

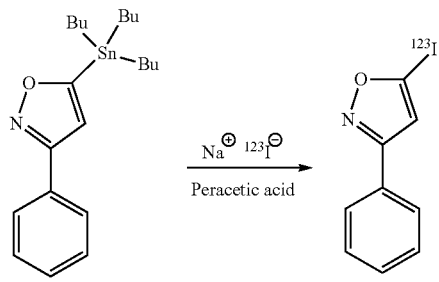

To sodium [$^{123}$I] iodide, received in 5-20 μL 0.05M sodium hydroxide is added ammonium acetate buffer (100 μL pH 4.0, 0.2M), sodium [$^{127}$I] iodide (10 μL, 1 mM solution in 0.01M sodium hydroxide, $1\times10^{-8}$ moles), peracetic acid (PAA) solution (10 μL 1 mM solution, $1\times10^{-8}$ moles) and finally, 3-phenyl-5-tributylstannyl-isoxazole (Example 6; 43 μg, $1\times10^{-7}$ moles) dissolved in acetonitrile. The reaction mixture is incubated at room temperature for 15 minutes prior to purification by HPLC.

Example 8

Preparation of 10-(4-Iodo-[1,2,3]-triazol-1-yl)-decanoic acid (Prophetic Example)

Step (a): Preparation of 10-(4-azido-[1,2,3]triazol-1-yl)-decanoic acid

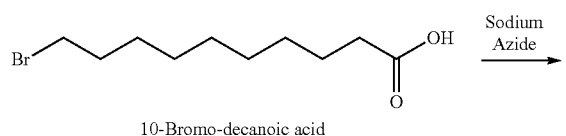

10-Bromodecanoic acid (2.51 g, 10 mmol) in acetone (50 mL) is treated with sodium azide (0.75 g, 11 mmol) at reflux for 2 h. The reaction is then concentrated in vacuo to a gum that is partitioned between ethyl acetate (50 mL) and water (50 mL). The organic phase is separated, dried over sodium sulfate and concentrated in vacuo to give 10-azidodecanoic acid (2.02 g, 95%).

Step (b): Preparation of 10-(4-tributylstannyl-[1,2,3]triazol-yl)-decanoic acid

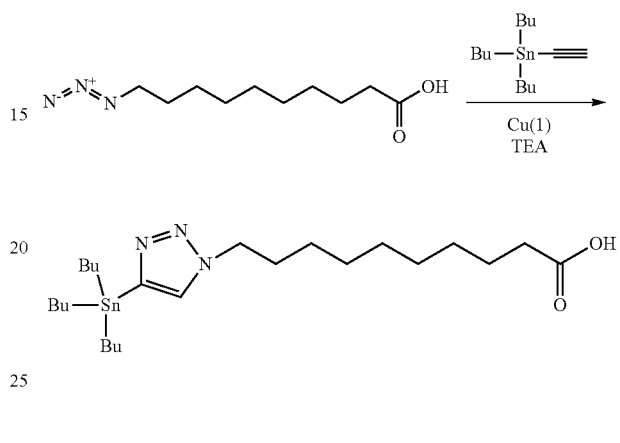

10-Azidodecanoic acid (2.0 g, 9.5 mmol) in THF (50 mL) is treated with tributylstannyl acetylene (2.99 g, 9.5 mmol) copper(I)iodide (90 mg 0.47 mmol) and triethylamine (256 mg, 2.54 mmol) at room temperature with constant stirring for 24 h. The reaction is then filtered through celite and concentrated in vacuo to a gum, and then chromatographed on silica in a gradient of 10-40% ethyl acetate in petrol. The main fraction is collected and concentrated in vacuo to give 10-(4-tributylstannyl-[1,2,3]triazol-1-yl)-decanoic acid (3.22 g, 0.8 mmol).

Step (c): Preparation of 10-(4-iodo-[1,2,3]triazol-1-yl)-decanoic acid

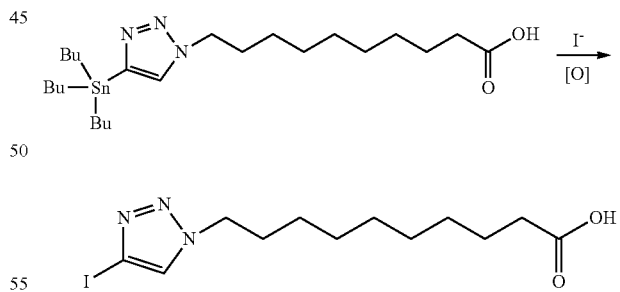

To sodium [$^{123}$I] iodide, received in 5-20 μL 0.05M sodium hydroxide is added ammonium acetate buffer (100 μL pH 4.0, 0.2M), sodium [$^{127}$I] iodide (10 μL, 1 mM solution in 0.01M sodium hydroxide, $1\times10^{-8}$ moles), peracetic acid (PAA) solution (10 μL 1 mM solution, $1\times10^{-8}$ moles) and finally 10-(4-tributylstannyl-[1,2,3]triazol-1-yl)-decanoic acid solution in ethanol or acetonitrile (53 μg, $1\times10^{-7}$ moles). The reaction mixture is allowed to stand at room temperature for 15 minutes prior to HPLC purification of the iodinated product 10-(4-iodo-[1,2,3]triazol-1-yl)-decanoic acid.

Example 9

Preparation of 10-(5-Iodo isoxazol-3-yl)-decanoic acid (Prophetic Example)

Step (a): Preparation of 11[(E)-hydroxyimino-decanoic acid

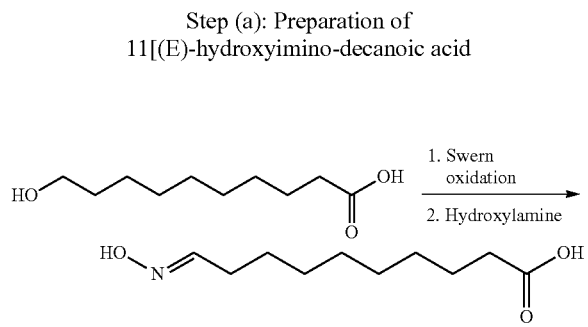

A solution of dimethyl sulfoxide (1.17 g, 15 mmol) in dichloromethane (50 mL) is cooled to −30° C. and treated with oxalyl chloride (1.92 g, 15 mmol). The reaction mixture is then treated with 10-hydroxydecanoic acid (2.06 g, 10 mmol) in dichloromethane (50 mL) and allowed to warm to room temperature over a period of 2 h. The reaction is then washed with water (2×50 mL). The organic layer is dried over sodium sulfate and then treated with hydroxylamine hydrochloride (1.03 g 15 mmol) and sodium hydroxide (0.6 g in 10 mL water) and stirred vigorously for 1 h. The organic phase is then separated dried over sodium sulfate and concentrated in vacuo to give 11[(E)-hydroxyimino-decanoic acid (1.8 g, 9.0 mmol).

Step (b): Preparation of 10-(5-tributylstanyl-isoxazol-3-yl)-decanoic acid

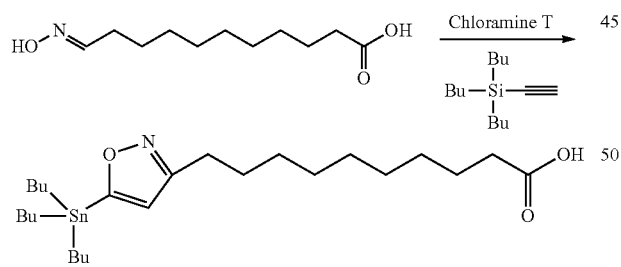

11[(E)-Hydroxyimino-decanoic acid (1.8 g, 9.0 mmol) is dissolved in acetonitrile (30 ml) and the solution cooled to 0° C. and then treated with a solution of chloramine-T trihydrate (2.52 g, 9.0 mmol) in water (10 mL). The reaction is allowed to warm to room temperature over a period of 25 minutes. To the resulting nitrile oxide solution is added tributyl(ethynyl)stannane (2.83 g, 9.0 mmol), copper iodide (100 mg, 0.5 mmol) and triethylamine (50 mg, 0.5 mmol) and the reaction stirred at room temperature for 24 h. The reaction is then filtered through celite to remove the copper salts and concentrated in vacuo to a gum. The gum is then chromatographed on silica in a gradient of 10-30% ethyl acetate in petrol to give 10-(5-tributylstanyl-isoxazol-3-yl)-decanoic acid.

Step (c): Example 4: Preparation of 10-(5-iodo isoxazol-3-yl)-decanoic acid

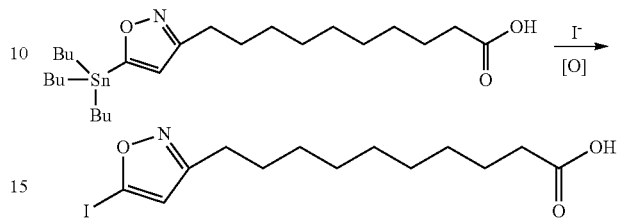

To sodium [$^{123}$I] iodide, received in 5-20 μL 0.05M sodium hydroxide is added ammonium acetate buffer (100 μL pH 4.0, 0.2M), sodium [$^{127}$I] iodide (10 μL, 1 mM solution in 0.01M sodium hydroxide, 1×10$^{-8}$ moles), peracetic acid (PAA) solution (10 μL 1 mM solution, 1×10$^{-8}$ moles) and finally 10-(5-tributylstannyl-isoxazol-3-yl)-decanoic acid solution in ethanol or acetonitrile (53 μg, 1×10$^{-7}$ moles). The reaction mixture is allowed to stand at room temperature for 15 minutes and the iodinated product 10-(4-iodo-[1,2,3]triazol-1-yl)-decanoic acid purified by HPLC.

What is claimed is:

1. A radioiodinated fatty acid of Formula (I):

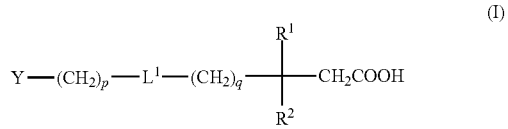

where:
R$^1$ and R$^2$ are independently H or C$_{1-2}$ alkyl;
Y is a Y$^2$ group:

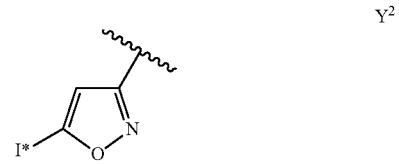

p and q are each independently integers of value 0 to 10 which are chosen such that [p+q] is in the range 10 to 16;
L$^1$ is a linker group of formula -(A)$_n$- where n is an integer of value 0 to 3, and each A group is independently chosen from —CH$_2$—, —O—, —S— and —C$_6$H$_4$— with the proviso that L$^1$ does not comprise —O—O—, —S—S— or —O—S— linkages; and
I* is a radioisotope of iodine.

2. The radioiodinated fatty acid of claim 1, wherein I* is chosen from $^{123}$I, $^{124}$I or $^{131}$I.

3. The radioiodinated fatty acid of claim 1, where R$^1$ is CH$_3$ and R$^2$ is H.

4. The radioiodinated fatty acid of claim 1, where L$^1$ is chosen from —CH$_2$—, —O— and —S—.

5. The radioiodinated fatty acid of claim 1, where n=0, and [p+q] is in the range 11 to 13.

6. A radiopharmaceutical composition comprising an effective amount of the radioiodinated fatty acid of Formula (I) as defined in claim 1, together with a biocompatible carrier medium.

* * * * *